(12) United States Patent
Yoshimasa

(10) Patent No.: US 7,125,401 B2
(45) Date of Patent: Oct. 24, 2006

(54) ABSORBENT ARTICLE WITH FRONT AND REAR SUPPORTING MEMBERS

(75) Inventor: Wataru Yoshimasa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 480 days.

(21) Appl. No.: 10/341,980

(22) Filed: Jan. 14, 2003

(65) Prior Publication Data

US 2003/0135188 A1     Jul. 17, 2003

(30) Foreign Application Priority Data

Jan. 15, 2002    (JP)    ............................. 2002-005521

(51) Int. Cl.
*A61F 13/15*    (2006.01)

(52) U.S. Cl. ................. 604/392; 604/385.03; 604/393; 604/402

(58) Field of Classification Search ........... 604/385.01, 604/385.03, 386, 387, 389, 392, 385.21, 604/393, 397, 400, 401, 402; D24/124, 125
See application file for complete search history.

(56) References Cited

U.S. PATENT DOCUMENTS

| | | | |
|---|---|---|---|
| 1,919,124 A * | 7/1933 | Panullo | .................. 604/401 |
| 3,185,394 A * | 5/1965 | Farrell | .......................... 239/36 |
| 3,575,174 A * | 4/1971 | Mogor | .................. 604/385.01 |
| 3,906,952 A | 9/1975 | Zamist | |
| 4,072,151 A | 2/1978 | Levine | |
| 4,484,919 A | 11/1984 | Sohn et al. | |
| 4,505,707 A * | 3/1985 | Feeney | ........................ 604/393 |
| 4,753,648 A | 6/1988 | Jackson | |
| D298,459 S * | 11/1988 | McCormick | ................ D24/125 |
| D365,877 S * | 1/1996 | Fraser et al. | ................ D24/125 |
| 6,461,341 B1 * | 10/2002 | Bennett | .................. 604/385.18 |
| D473,300 S * | 4/2003 | Llanos-Vega | .............. D24/125 |
| 6,613,031 B1 * | 9/2003 | Glasgow et al. | ....... 604/385.03 |
| 6,632,210 B1 * | 10/2003 | Glasgow et al. | ....... 604/385.17 |
| 6,755,808 B1 * | 6/2004 | Balogh et al. | ......... 604/385.28 |
| 2002/0193766 A1 * | 12/2002 | Gell et al. | ............. 604/385.03 |
| 2003/0120235 A1 * | 6/2003 | Boulanger | .................. 604/378 |
| 2003/0139721 A1 * | 7/2003 | Melius et al. | .......... 604/385.01 |

FOREIGN PATENT DOCUMENTS

| | | |
|---|---|---|
| EP | 0 945 110 A2 | 9/1999 |
| EP | 1 269 952 A2 | 1/2003 |
| EP | 1 327 433 A3 * | 1/2004 |
| JP | 3-101933 | 10/1991 |
| WO | WO-01/49232 A1 | 7/2001 |

OTHER PUBLICATIONS

Patent Abstracts of Japan, JP 09 117473, May 6, 1997, vol. 1997, No. 09, Abstract.

* cited by examiner

*Primary Examiner*—Tatyana Zalukaeva
*Assistant Examiner*—Michael G. Bogart
(74) *Attorney, Agent, or Firm*—Darby & Darby

(57) ABSTRACT

Disclosed is an absorbent article including: a main body portion having an ability to absorb and retain a liquid; a front support member extending forward beyond a front edge of the main body portion; and a rear support member extending rearward beyond a rear edge of the main body portion. The individual front and rear support members produce an elastic contractive force in a stretched state. The individual front and rear support members are provided with a pressure sensitive adhesive layer for securing each support member to the skin of a wearer.

16 Claims, 9 Drawing Sheets

ABSORBENT ARTICLE WITH FRONT AND REAR SUPPORTING MEMBERS

CROSS-REFERENCE TO RELATED APPLICATIONS

This application claims priority under 35 U.S.C. §119 from Japanese Patent Application No. 2002-005521, filed on Jan. 15, 2002.

BACKGROUND OF THE INVENTION

1. Field of the Invention

The present invention relates to an absorbent article of which a main body portion having an ability to absorb and retain a liquid hardly gets out of position once it comes into close contact with the crotch of the wearer's body.

2. Description of the Related Art

Absorbent articles to be used by women during a menstruation should be always kept in close contact with the vaginal opening for assuring absorption of menstrual blood.

Japanese Unexamined Utility-Model Publication No. H3-101933 (101933/1991) discloses an absorbent article comprising a main body portion having an absorbent core and elastically stretchable flaps. The flaps extend forward and rearward from longitudinally opposed-ends of the main body portion, and each flap has a slippage prevent member on its garment surface for facing an undergarment. This absorbent article is worn by stretching the flaps and fixing the slippage prevent members on an inner side of an undergarment such as short panty. During wear, the main body portion is forced against the vaginal opening of a wearer due to elasticity of the flaps, so that the main body portion can be kept in close contact with the vaginal opening of a wearer.

In the absorbent article disclosed in the above-identified publication, however, since the flaps are intended to be fixed on an undergarment for use, if the undergarment is loosened or stretched due to motion of the wearer's body or relative position of the undergarment and the wearer's body is changed, relative position of the absorbent article and the wearer's body may be changed. Thus, it is difficult to keep the absorbent article in close contact with the vaginal opening.

SUMMARY OF THE INVENTION

The present invention has been worked out in view of the shortcoming in the prior art set forth above. It is therefore an object of the present invention to provide an absorbent article which can be kept in close contact with the vaginal opening of a wearer without displacement.

According to the invention, there is provided an absorbent article comprising:

a main body portion having an ability to absorb and retain a liquid;

a front support member extending forward beyond a front edge of the main body portion; and a rear support member extending rearward beyond a rear edge of the main body portion, wherein the individual front and rear support members produce an elastic contractive force in a stretched state, and the individual front and rear support members are provided with means for securing each support member to the skin of a wearer.

The absorbent article of the present invention is worn by fixing the front and rear support members to the wearer's skin with the securing means. Since the front and rear support members are fixed to the wearer's skin, even if an undergarment is loosened or stretched due to motion of the wearer's body or relative position of the undergarment and the wearer's body is changed, the absorbent article can be kept in close contact with the vaginal opening. At this time, if the absorbent article is worn by fixing the support members in a stretched state, the main body portion is forced against the genital organ of a wearer due to an elastic contractive force of the front and rear support members, so that the main body portion comes into close contact with the vaginal opening of a wearer.

The main body portion may have a layer for blocking passage of a liquid toward a garment surface of the main body portion. In this case, since a liquid discharged from the wearer's body and absorbed and retained by the main body portion can be blocked by the layer, an undergarment such as short panty can be prevented from being soiled with the liquid. Alternatively, a garment surface of the main body portion may be permeable to liquid, at least in a central region thereof. If so, it is preferred to use the absorbent article as auxiliary means in combination with another absorbent article such as a sanitary napkin to be worn on an inner side of an undergarment. In this case, a liquid discharged from the wearer's body can be firstly absorbed by the main body portion of the absorbent article of the present invention in close contact with the vaginal opening. When a liquid is given in an amount in excess of a liquid retention capacity of the main body portion, an excess of liquid that cannot be retained by the main body portion is given to the other absorbent article through the garment surface of the main body portion and then absorbed. Therefore, even if the absorbent article of the present invention is thin or the other absorbent article is thin, much liquid can be absorbed.

The rear support member may be joined at one end to a garment surface of the main body portion, wherein the joined end of the rear support member may be positioned in a region ahead of a transversely extending centerline of the main body portion. With such construction, since the main body portion can be deformed by the rear support member to protrude toward the vaginal opening of a wearer, the main body portion can be readily brought into close contact with the vaginal opening.

Preferably, the rear support member has a width of equal to or less than 30 mm, within a region of a predetermined length extending rearward from the rear edge of the main body portion, so that the rear support member can easily fit in the gluteal fold. If the rear support member fits in the gluteal fold, the rear support member hardly gets out of the buttocks even when the wearer's body is moved. Therefore, the position of the main body portion in close contact wit the wearer's body can be easily stabilized. Behind the region of a predetermined length, preferably, the rear support member has a region which is gradually widened and provided at a location of a maximum width with the securing means. In this case, since the securing means can also be sufficiently widened, the rear support member can be stably fixed to the wearer's skin.

At least one of the front and rear support members may comprise at least two separate parts individually extending from the main body portion. In this case, since an external force given to the front support member and/or the rear support member in accordance with motion of the wearer's body can be distributed, the main body portion can be effectively prevented from getting out of position.

Preferably, when the front and rear support members are fully stretched, a distance between the securing means of the front support member and the securing means of the rear support member increases by at least 1.2 times that before stretch. Preferably, when the distance between the securing means of the front support member and the securing means of the rear support member is 1.2 times that before stretch, an elastic contractive force acting between the securing means of the front support member and the securing means of the rear support member is equal to or less than 1960 mN. If the elastic contractive force is equal to or less than 1960 mN, the support members fixed to the wearer's body in a stretched state can be prevented from giving an excessively oppressive sensation to the wearer's body, although the main body portion can be kept in close contact with the vaginal opening. In this case, preferably, when in close contact with the human skin, each securing means has a shear strength of greater than 1960 mN. If the shear strength is equal to or less than 1960 mN, the securing means that are fixed to the wearer's body while the support members are stretched may possibly slip off the wearer's skin during use.

Preferably, each securing means has a peel strength of equal to or less than 0.49 N per 25 mm width. If the peel strength is greater than the above-mentioned value, the wearer may possibly feel pain when the securing means is peeled off.

BRIEF DESCRIPTION OF THE DRAWINGS

The present invention will be understood more fully from the detailed description given hereinafter and from the accompanying drawings of the preferred embodiments of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
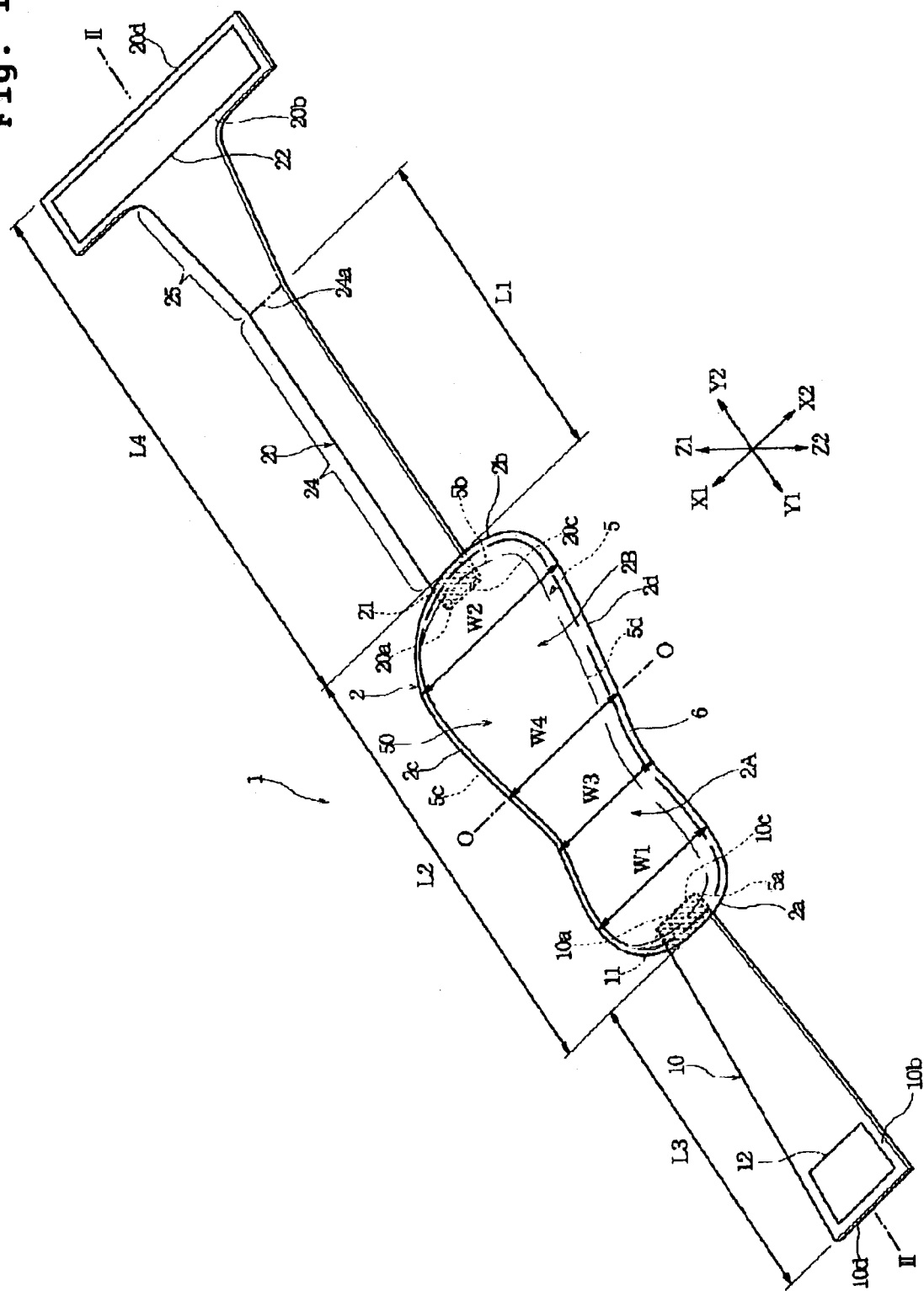
FIG. 1 is a perspective view showing an absorbent article according to a first embodiment of the present invention.
Figure 2A:
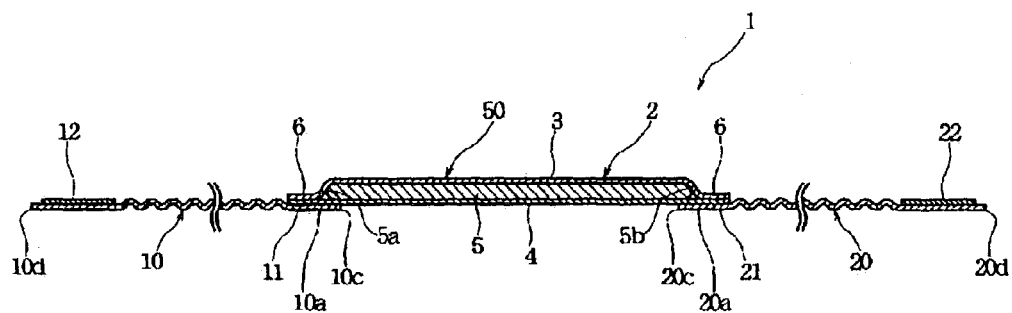
FIG. 2A is a sectional view taken along line II—II of FIG. 1.
Figure 2B:
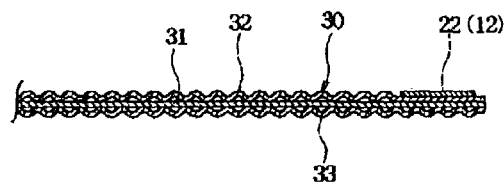
FIG. 2B is an enlarged view of a portion of FIG. 2A.

FIG. 1 is a perspective view showing an absorbent article 1 to be worn by a woman during a menstruation according to a first embodiment of the present invention; FIG. 2A is a sectional view taken along line II—II of FIG. 1; FIG. 2B is an enlarged view of a portion of FIG. 2A; and FIG. 3 is a sectional view showing a state where a front support member and a rear support member are folded.

Figure 3:
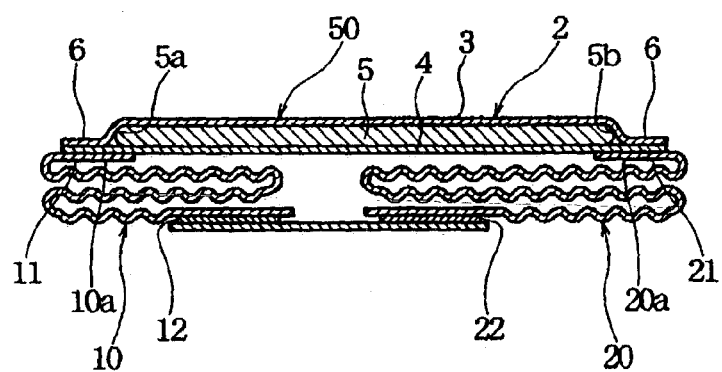
FIG. 3 is a sectional view showing a state where a front support member and a rear support member of the absorbent article of FIG. 1 are folded.

The absorbent article 1 of FIGS. 1 to 3 is to be attached to the genital organ of a woman during a menstruation for absorbing and retaining a discharged body fluid such as menstrual blood. The absorbent article 1 comprises a main body portion 2, a front support member 10 and a rear support member 20. It should be noted that individual components of the absorbent article 1 have a body surface and a garment-surface. As used herein, "body surface" means that surface of the components which is intended to be worn toward or adjacent to the body of a wearer, while the "garment surface" is on the opposite side and is intended to be worn toward or placed adjacent to an undergarment when the absorbent article is worn.

As shown in FIG. 1, the main body portion 2 is elongated in a Y-direction (Y1-Y2 direction) so that its maximum dimension in an X-direction (X1-X2 direction) is smaller than that in the Y-direction. It should be noted that a Z-direction (Z1-Z2 direction) is perpendicular to an XY-plane. Hereinbelow, a dimension in the X-direction is referred to as a "width", a dimension in the Y-direction is referred to as a "length" and a dimension in the Z-direction is referred to as a "thickness". The main body portion 2 is of an hour-glass shape having a generally arcuate front edge 2a, a rear edge 2b that is generally arcuate as well, and right and left side edges 2c and 2d. The distance between the right and left side edges 2c and 2d, i.e., the width of the main body portion 2 varies with the location. More specifically, the width of the main body portion 2 varies to satisfy the following relationship: W2>W1>W3. Here, the main body portion 2 has a front region 2A ahead of a transversely extending centerline O—O of the main body portion 2 and a rear region 2B behind the transversely extending centerline O—O of the main body portion 2. The constricted portion having the width W3 is slightly offset from the centerline O—O toward the front edge 2a.

As shown in the sectional view of FIG. 2A, the main body portion 2 comprises: a liquid permeable topsheet 3; a liquid impermeable backsheet 4; and an absorbent layer (absorbent core) 5 having an ability to absorb a liquid and retain the absorbed liquid between the topsheet 3 and the backsheet 4.

The topsheet 3 is intended to come into direct contact with the genital organ of a wearer. Therefore, the body surface (the surface appearing in FIG. 1) of the topsheet 3 forms a liquid-receiving surface 50 of the main body portion 2. In the embodiment shown, since the absorbent layer 5 is of a constant thickness, the liquid-receiving surface 50 is substantially flat.

In the embodiment shown, the topsheet 3 and the backsheet 4 are of the same dimensions, so that front edges, rear edges and right and left side edges of the topsheet 3 and the backsheet 4 coincide with the front edge 2a, the rear edge 2b and the right and left side edges 2c and 2d, respectively.

The absorbent layer 5 is of a given thickness and shaped to have a front edge 5a, a rear edge 5b and right and left side edges 5c and 5d, as shown in FIG. 1. The front edge 5a, the rear edge 5b and the right and left side edges 5c and 5d of the absorbent layer 5 are similar in shape to but spaced 3 to 10 mm inwardly apart from the front edge 2a, the rear edge 2b and the right and left side edges 2c and 2d of the main body portion 2, respectively. Outside the front edge 5a, the rear edge 5b and the right and left side edges 5c and 5d of the absorbent layer 5, the topsheet 3 and the backsheet 4 are joined to each other through a hot-melt type adhesive or by heat-sealing, thereby forming a joined portion 6.

The front support member 10 extends forward (in the Y1 direction in FIG. 1) beyond the front edge 2a of the main body portion 2; and the rear support member 20 extends rearward (in the Y2 direction in FIG. 1) beyond the rear edge 2b of the main body portion 2.

The front support member 10 has longitudinally opposed front and rear edges 10d and 10c. A rear end region 10a of the front support member 10 adjacent to the rear edge 10c is laid on the garment surface of the main body portion 2 with the rear edge 10c slightly spaced inward apart from the front edge 2a of the main body portion 2. The rear end region 10a is joined to the garment surface of the main body portion 2 through a hot-melt type adhesive or by heat-sealing, thereby forming a joined portion 11. On the body surface of a front end region 10b of the front support member 10 adjacent to the front edge 10d, on the other hand, there is provided a pressure sensitive adhesive layer 12 as means for securing the front support member 10 to the skin of a wearer. The front support member 10 is of a tapered shape, wherein the width is gradually increased from the rear edge 10c toward the front edge 10d.

The rear support member 20 has longitudinally opposed front and rear edges 20c and 20d. A front end region 20a of the rear support member 20 adjacent to the front edge 20c is laid on the garment surface of the main body portion 2 with the front edge 20c slightly spaced inward apart from the rear edge 2b of the main body portion 2. The front end region 20a is joined to the garment surface of the main body portion 2 through a hot-melt type adhesive or by heat-sealing, thereby forming a joined portion 21. On the body surface of a rear end region 20b of the rear support member 20 adjacent to the rear edge 20d, on the other hand, there is provided a pressure sensitive adhesive layer 22 as means for securing the rear support member 20 to the skin of a wearer. Between the front end region 20a and the rear end region 20b, the rear support member 20 has a region 24 for fitting in the gluteal fold of a wearer (hereinafter referred to as a gluteal fold-fitting region 24), which extends rearward from the rear edge 2b of the main body portion 2 over a length L1 to have a constant width (equal to or less than 30 mm). Moreover, there is provided a tapered region 25, in which the width is gradually increased from a rear edge 24a of the gluteal fold-fitting region 24 toward the rear end region 20b.

Both the front support member 10 and the rear support member 20 are formed of a laminate sheet 30 of FIG. 2B.

The laminate sheet 30 comprises a substantially unstretchable first auxiliary sheet 32 to appear on the body surface of each support member, a substantially unstretchable second auxiliary sheet 33 to appear on the garment surface of each support member, and a plurality of string- or strip-shaped elastic members 31 disposed between the first and second auxiliary sheets 32 and 33. The elastic members 31 are in parallel relationship with each other to extend from the rear edge 10c to the front edge 10d in the front support member 10 and from the front edge 20c to the rear edge 20d in the rear support member 20. The elastic members 31 are fixed in a stretched state to the first and second auxiliary sheets 32 and 33 through a hot-melt type adhesive or the like. There-fore, the front and rear support members 10 and 20 can produce an elastic contractive force in a stretched state.

The topsheet 3 of the main body portion 2 is permeable to liquid and may be formed of a through-air bonded nonwoven fabric comprising bicomponent synthetic fibers of polyethylene and polypropylene, a spunlaced nonwoven fabric comprising the bicomponent synthetic fibers, a resin film formed with a number of liquid passage holes, or the like. The above-mentioned nonwoven fabrics may also be formed with liquid passage holes. The resin film formed with a number of liquid passage holes may be laminated to any of the above-mentioned nonwoven fabrics. In order to improve the feel, the topsheet 3 is preferably creped or embossed.

The backsheet 4 of the main body portion 2 is impermeable to liquid and may be formed of a resin film of polyethylene, a laminate of the resin film and a nonwoven fabric, or the like.

The absorbent layer 5 of the main body portion 2 has an ability to absorb a liquid and retain the absorbed liquid and may be formed of a mixture of comminuted pulp and superabsorbent polymer (SAP), a sheet having SAP between two sheets of liquid absorbent paper, air-laid pulp, expanded cellulose, or the like.

The elastic members 31 used in the front and rear support members 10 and 20 may be formed of natural rubber, synthetic rubber, polyurethane elastic yarn, polyurethane foam, or the like. The first and second auxiliary sheets 32 and 33 may be formed of a nonwoven fabric of a low density.

For the pressure sensitive adhesive layers 12 and 22, preferably used is a gel that has a water-soluble material as main component. For example, the gel may be formed by mixing a copolymer of polyacrylic acid and sodium poly acrylate, aluminum hydroxide, tartaric acid, glycerin and water, followed by stirring. It should be noted that the pressure sensitive adhesive layers 12 and 22 should not be limited to such a gel that has a water-soluble material as main component, but may also include a gel that has a water-insoluble material as main component. For example, a material prepared by heating and melting a blockcopolymer comprising styrene and isoprene (having a structure of styrene polymer-isoprene polymer-styrene polymer), a paraffin oil and a tackifier, may be used.

Before use, the absorbent article 1 is individually packaged in a packaging film (not shown), while the front and rear support members 10 and 20 are folded on the garment surface of the main body portion 2 and the pressure sensitive adhesive layers 12 and 22 are covered with a release sheet 40, as shown in FIG. 3.

Upon use, after the release sheet 40 is removed from the pressure sensitive adhesive layers 12 and 22, the front support member 10 is unfolded to extend forward of the main body portion 2 and the rear support member 20 is unfolded to extend rearward of the main body portion 2.

Then, after the topsheet 3 of the main body portion 2 is brought into contact with the genital organ of a wearer, the front support member 10 is stretched forward of the main body portion 2 and the pressure sensitive adhesive layer 12 is adhered to the wearer's skin in the lower abdominal region. Since the front support member 10 is configured to gradually increase the width toward the front edge 10d, the front support member 10 can decrease a pressure to the lower abdominal region of a wearer. In addition, since the area of the pressure sensitive adhesive layer 12 can be increased, the front support member 10 can be firmly fixed to the wearer's skin.

On the other hand, the rear support member 20 is stretched rearward of the main body portion 2 and the pressure sensitive adhesive layer 22 is fixed to the wearer's skin in the lower lumbar region above the gluteal fold. At this time, the gluteal fold-fitting region 24 of the rear support member 20 fits in the gluteal fold of a wearer, and the tapered region 25, in which the width is gradually increased, comes into contact with a portion of the wearer's body where the gluteal fold becomes shallow. Thus, the rear support member 20 can conform to the body shape of a wearer.

In the case where the front and rear support members 10 and 20 are fixed to the wearer's skin in a stretched state, the main body portion 2 is forced against the genital organ of a wearer due to an elastic contractive force of the support members 10 and 20 so that the main body portion 2 comes into close contact with the vaginal opening of a wearer. In addition, since the front and rear support members 10 and 20 are fixed on the wearer's body through the pressure sensitive adhesive layers 12 and 22, even if an undergarment is loosened, stretched or displaced due to motion of the wearer's body, the main body portion 2 can be certainly kept in close contact with the vaginal opening without being affected by motion of the undergarment.

In addition to the above-mentioned advantages, the front and rear support members 10 and 20 fixed on the lower abdominal region and the lower lumbar region through the pressure sensitive adhesive layers 12 and 22 can be flexibly deformed when the wearer's body is moved, thereby absorbing a force caused by motion of the wearer's body. Therefore, the main body portion 2 hardly gets out of position.

As one property of the main body portion 2 with respect to an external force, it is preferred that when a load is applied onto a flat plate that covers the entire liquid-receiving surface 50 of the main body portion 2 in a dry state to apply a pressure of 1471 Pa, the liquid-receiving surface 50 is pushed down (depressed) by at least 5 mm under the above-mentioned pressure. If the amount of depression under the above-mentioned pressure is less than 5 mm, it becomes difficult for the liquid-receiving surface 50 to conform to unevenness of the genital organ of a wearer, so that an adhesion between the main body portion 2 and the vaginal opening will be deteriorated.

The term "dry state" as used herein refers to a state where the absorbent article 1 is allowed to stand for at least 30 minutes in an atmosphere having a temperature of 20±2° C. and a relative humidity of 65±2%.

The front and rear support members 10 and 20 can be stretched until the wrinkles of FIG. 2B are smoothed out of the first and second auxiliary sheet 32 and 33. Here, when the front and rear support members 10 and 20 are fully stretched by pulling the pressure sensitive adhesive layers 12 and 22 in the Y1 and Y2 directions, respectively, a distance between the pressure sensitive adhesive layers 12 and 22 increases by preferably at least 1.2 times, more preferably at least 1.3 times that before stretch. When the distance between the pressure sensitive adhesive layers 12 and 22 is 1.2 times that before stretch, moreover, an elastic contractive force acting between the pressure sensitive adhesive layers 12 and 22 is preferably equal to or less than 1960 mN. It is also preferred that an elastic contractive force acting between the pressure sensitive adhesive layers 12 and 22 when the front and rear support members 10 and 20 are fully stretched is equal to or less than 1960 mN.

In the case where the distance between the pressure sensitive adhesive layers 12 and 22 can increase by at least 1.2 times (more preferably 1.3 times) that before stretch and the elastic contractive force acting between the pressure sensitive adhesive layers 12 and 22 at this time is equal to or less than 1960 mN, the pressure sensitive adhesive layers 12 and 22 hardly give an excessive pulling force to the portions of the skin on which they are fixed. Therefore, the main body portion 2 can be prevented from being displaced forward or rearward from the vaginal opening due to the elastic contractive force of the front and rear support members 10 and 20, as well as the main body portion 2, the front support member 12 and the rear support member 22 can be prevented from giving an excessively oppressive sensation to the wearer's body.

In order to keep the pressure sensitive adhesive layers 12 and 22 fixed on the wearer's skin in a state where the front and rear support members 10 and 20 are stretched, the pressure sensitive adhesive layers 12 and 22 preferably have a shear strength of greater than 1960 mN.

The term "shear strength" refers to a value measured by the following method.

Figure 4B:
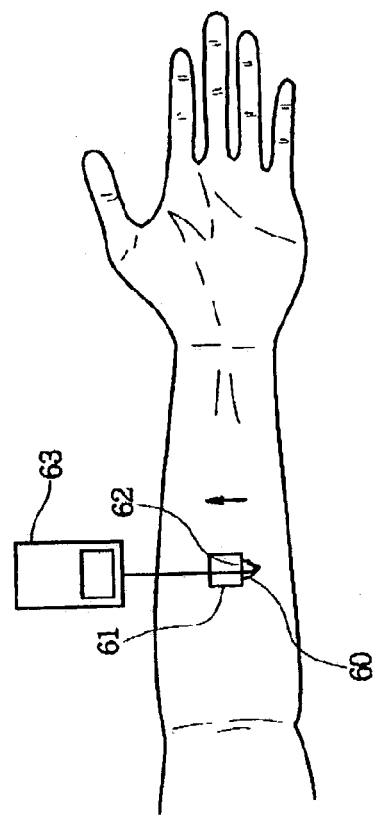
FIG. 4B is an illustration showing a method of measuring a peel strength.
Figure 4A:
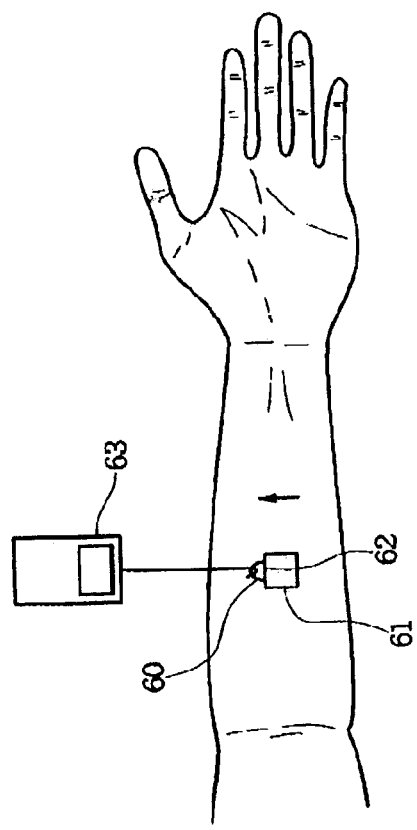
FIG. 4A is an illustration showing a method of measuring a shear strength.

FIG. 4A is an illustration showing a method of measuring the shear strength. An adhesive identical to that forming the pressure sensitive adhesive layers 12 and 22 is applied to a nonwoven fabric identical to that forming the first and second auxiliary sheets 32 and 33 to have the same thickness as the pressure sensitive adhesive layers 12 and 22. A sample 61 is obtained by cutting the nonwoven fabric coated with the adhesive into a square piece having a size of 25×25 mm and providing a loop 60 on one side 62 of the square piece.

The sample 61 is fixed by adhering the adhesive to the inside of the human forearm. At this time, the side 62 having the loop 60 is faced toward the shearing direction (indicated by an arrow in the drawing). After standing 10 minutes, a hook attached to a contact of Digital Force Gauge 63 "SHIMPO FGC-0.2" manufactured by NIDEC-SHIMPO CORPORATION, Japan, is engaged to the loop 60 of the sample 61, and gradually pulled in the shearing direction. A maximum load indicated by the Digital Force Gauge when the sampled slips off is read.

The shear strength of the individual pressure sensitive adhesive layers 12 and 22 is expressed by the maximum load×{an actual area of each pressure sensitive adhesive layer $(mm^2)/(25\ mm \times 25\ mm)$}.

On the other hand, the pressure sensitive adhesive layers 12 and 22 preferably have a peel strength of equal to or less than 0.49 N per 25 mm width. If the peel strength is greater than the above-mentioned value, the pressure sensitive adhesive layers 12 and 22 are liable to cause pain when they are peeled from the wearer's skin.

The peel strength refers to a value measured by the following method.

FIG. 4B is an illustration showing a method of measuring the peel strength. The sample 61 is fixed by adhering the adhesive to the inside of the human forearm. At this time, the side 62 having the loop 60 is faced toward the opposite direction to the pulling direction. After standing 10 minutes, the hook attached to the contact of Digital Force Gauge 63 "SHIMPO FGC-0.2" manufactured by NIDEC-SHIMPO CORPORATION, Japan, is engaged to the loop 60 of the sample 61, and gradually pulled upward as seen in the drawing (in a direction parallel to the plane of the sample 61). A maximum load indicated by the Digital Force Gauge when the sampled 61 is peeled off is read, and this maximum load is taken as the peel strength per 25 mm width.

A length L2 of the main body portion 2 is preferably from 90 to 300 mm, more preferably from 90 to 150 mm. If the length L2 is less than 90 mm, it is difficult to cover the labia over the entire length thereof, so that leakage of menstrual blood is easy to cause. If the length L2 is greater than 300 mm, on the other hand, the main body portion 2 is uncomfortable to wear. Here, if the length L2 is equal to or less than 150 mm, the main body portion 2 can be comfortably worn without causing a feeling that something is wrong.

A width W4 of the main body portion 2 along the centerline O—O is preferably from 30 to 70 mm. If the width W4 is less than 30 mm, it is difficult to cover the labia over the entire width thereof, so that leakage of menstrual blood is easy to cause. If the width W4 is greater than 70 mm, on the other hand, the right side edge 2c and the left side edge 2d of the main body portion 2 are transversely compressed by the inside of the thighs of a wearer during wear to produce a strain in the main body portion 2, so that leakage of menstrual blood is easy to cause.

A length L3 from the front edge 2a of the main body portion 2 to the front edge 10d of the front support member 10 is preferably set such that when the distance between the pressure sensitive adhesive layers 12 and 22 increases by 1.2 times that before stretch, the pressure sensitive adhesive layer 12 can adhere to the wearer's skin in a region having no pubic hair. With such construction, the pressure sensitive adhesive layer 12 can be firmly fixed, as well as can be prevented from causing pain when it is peeled off.

A length L4 from the rear edge 2b of the main body portion 2 to the rear edge 20d of the rear support member 20 is preferably set such that when the distance between the pressure sensitive adhesive layers 12 and 22 increases by 1.2 times that before stretch, the pressure sensitive adhesive layer 22 can adhere to the wearer's skin in the lower lumbar region above the gluteal fold, so as not to be affected by motion of the wearer's body.

Therefore, the lengths L3 and L4 are preferably set within the above-mentioned ranges in accordance with the length L2 of the main body portion 2.

Figure 5:
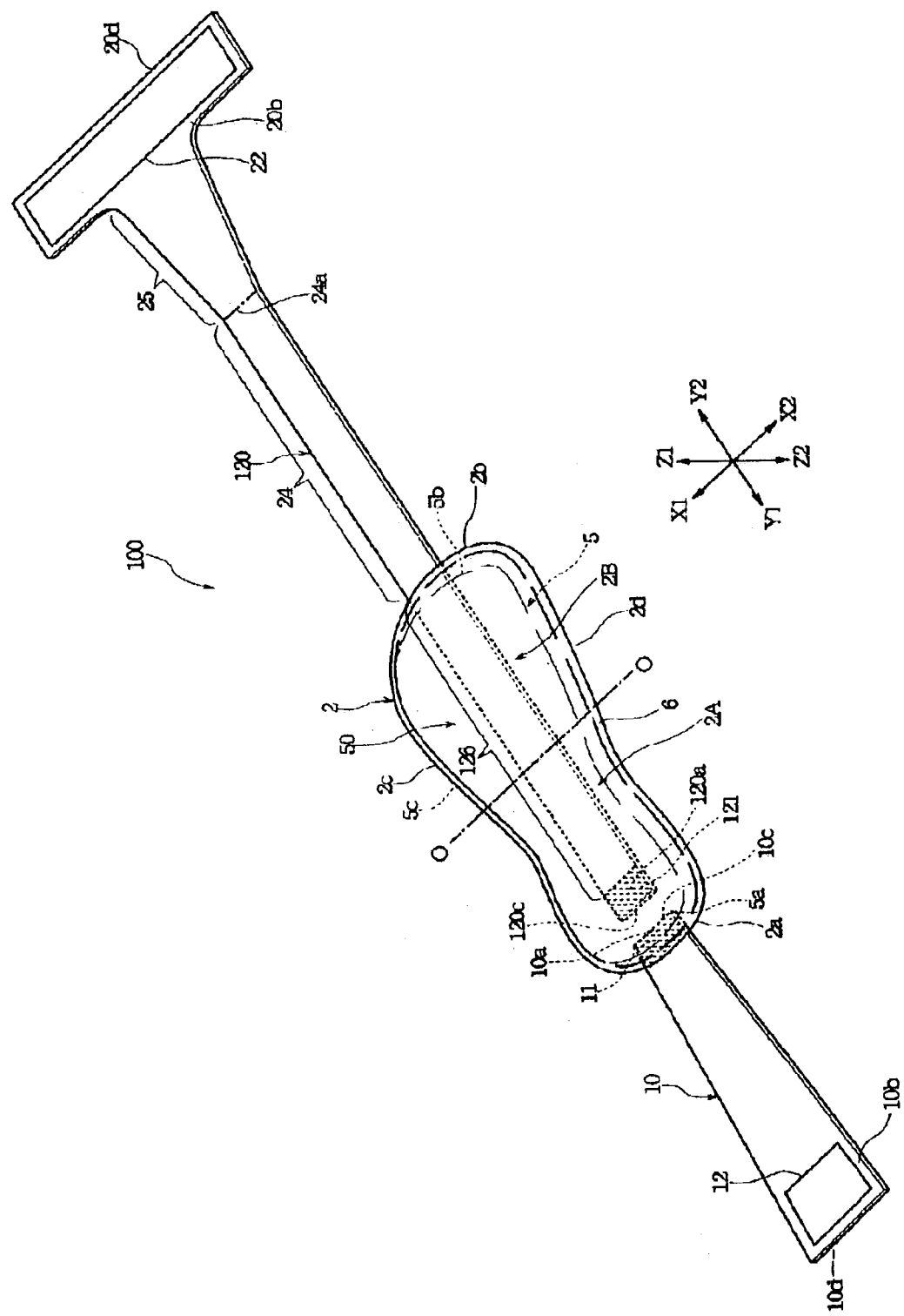
FIG. 5 is a perspective view showing an absorbent article according to a second embodiment of the present invention.

FIG. 5 is a perspective view showing an absorbent article 100 according to a second embodiment of the present invention. Here, the detailed description of the portions having the same constructions as those of the absorbent article 1 shown in FIGS. 1 to 3 will be omitted by designating them by the common reference numerals.

In the absorbent article 100 of FIG. 5, a rear support member 120 is extended to have a front edge 120c in the front region 2A of the main body portion 2 ahead of the centerline O—O. The rear support member 120 is joined at a front end region 120a to the garment surface of the backsheet 4 through a hot-melt type adhesive or by heat-sealing, thereby forming a joined portion 121. Thus, the rear support member 120 has a free region 126 that is located below the main body portion 2 to extend from the joined portion 121 to the rear edge 2b but is not joined to the backsheet 4. Behind the free region 126, the gluteal fold-fitting region 24 is continuously extended rearward from the rear edge 2b of the main body portion 2. The free region 126 and the gluteal fold-fitting region 24 have the same width.

During wear, since the elastic contractive force of the rear support member 120 acts on the free region 126, the main body portion 2 is pushed along its longitudinally extending centerline toward the genital organ of a wearer by the free region 126. Therefore, the main body portion 2 is deformed to protrude toward the genital organ of a wearer, so that the main body portion 2 can easily come into close contact with the vaginal opening of a wearer.

Although the free region 126 is not joined to the backsheet 4 in the second embodiment, it is possible to join the free region 126 to the backsheet 4 of the main body portion 2 through an adhesive or by heat-sealing. It is also possible that the front edge 120c of the rear support member 120 is fixed in the vicinity of the rear edge 2b of the main body portion 2, as in the first embodiment, but the front support member 10 is extended to have its rear edge 10c fixed on the backsheet 4 in the rear region 2B of the main body portion 2. Even with such construction, the main body portion 2 can be easily deformed to protrude. In the second embodiment, however, since the free region 126 of the rear support member 120 travels the length of the rear region 2B of the main body portion 2, as shown in FIG. 5, the rear region 2B can be easily deformed to protrude, so that the rear region 2B can be easily brought into close contact with the area from the vaginal opening to the anus, effectively preventing rearward liquid leakage.

Figure 6:
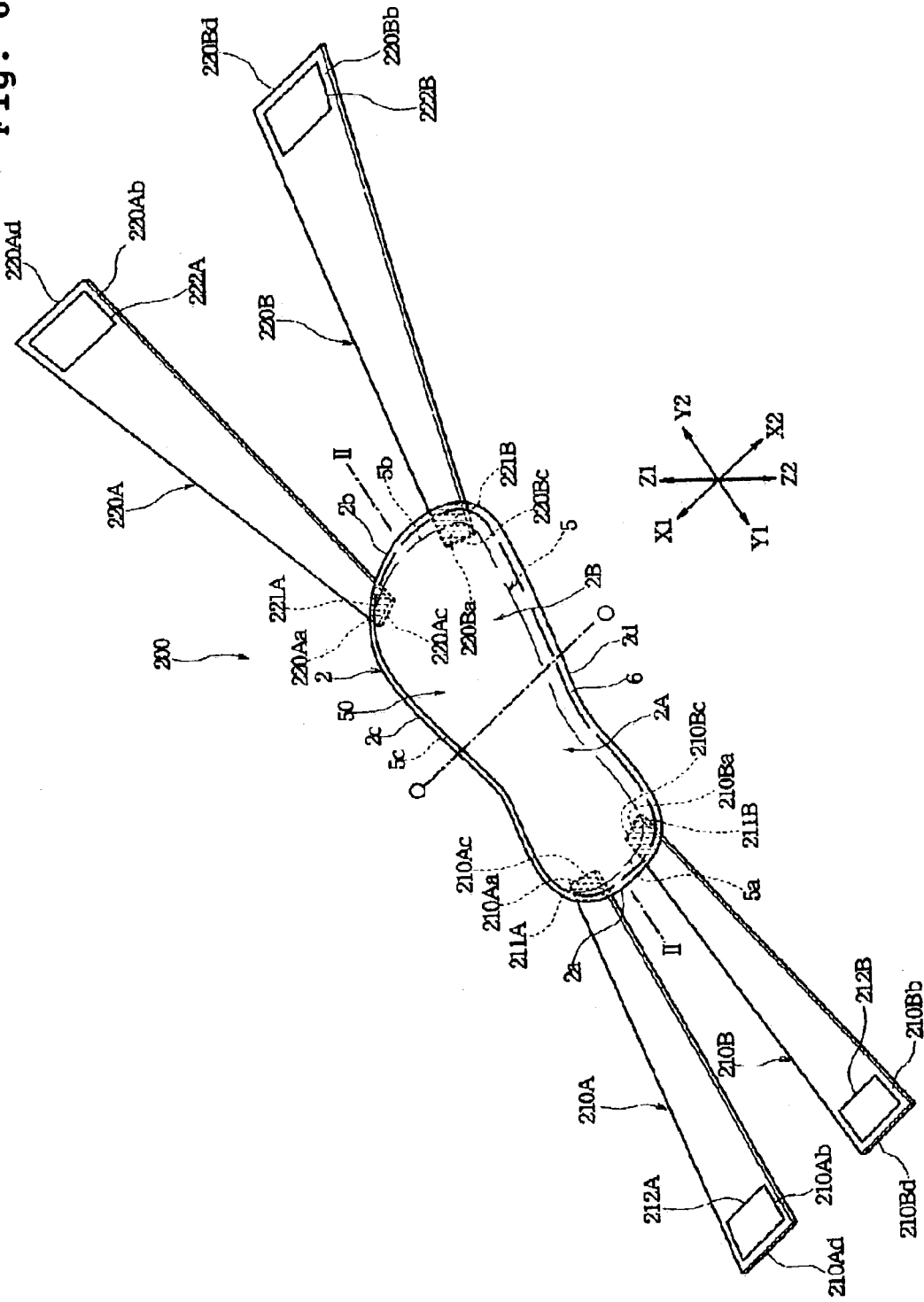
FIG. 6 is a perspective view showing an absorbent article according to a third embodiment of the present invention.

FIG. 6 is a perspective view showing an absorbent article 200 according to a third embodiment of the present invention. Here, the detailed description of the portions having the same constructions as those of the absorbent article 1 shown in FIGS. 1 to 3 will be omitted by designating them by the common reference numerals.

The absorbent article 200 of FIG. 6 has two front support members 210A and 210B and two rear support members 220A and 220B.

In the right half of the main body portion 2 between the longitudinally extending centerline II—II and the right side edge 2c, a rear end region 210Aa of the front support member 210A is joined to the garment surface of the main body portion 2 through a hot-melt type adhesive or by heat-sealing, thereby forming a joined portion 211A. On the body surface of a front end region 210Ab of the front support member 210A, there is provided a pressure sensitive adhesive layer 212A as means for securing the front support member 210A to the skin of a wearer. The front support member 210A is of a tapered shape, wherein the width is gradually increased from a rear edge 210Ac toward a front edge 210Ad.

In the left half of the main body portion 2 between the longitudinally extending centerline II—II and the left side edge 2d, a rear end region 210Ba of the front support member 210B is joined to the garment surface of the main body portion 2 through a hot-melt type adhesive or by heat-sealing, thereby forming a joined portion 211B. On the body surface of a front end region 210Bb of the front support member 210B, there is provided a pressure sensitive adhesive layer 212B as means for securing the front support member 210B to the skin of a wearer. The front support member 210B is also of a tapered shape, wherein the width is gradually increased from a rear edge 210Bc toward a front edge 210Bd.

Inside the rear edge 2b, a front end region 220Aa of the rear support member 220A and a front end region 220Ba of the rear support member 220B are respectively joined to the right and left halves of the main body portion 2 through a hot-melt type adhesive or by heat-stealing, thereby forming joined portions 221A and 221B. A pressure sensitive adhesive layer 222A is provided on the body surface of a rear end region 220Ab of the rear support member 220A, and a pressure sensitive adhesive layer 222B is provided on the body surface of a rear end region 220Bb of the rear support member 220B. The individual rear support members 220A and 220B are of a tapered shape, wherein the width is gradually increased from a front edge 220Ac, 220Bc toward a rear edge 220Ad, 220Bd.

Figure 7A:
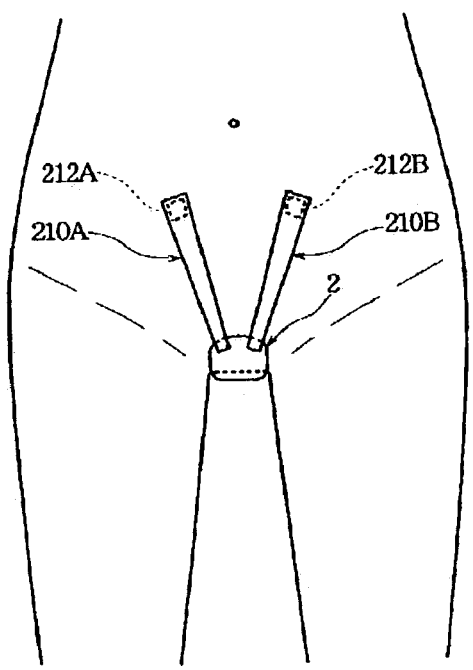
FIG. 7A shows a state where the absorbent article of FIG. 6 is worn, from the front of the wearer's body.
Figure 7B:
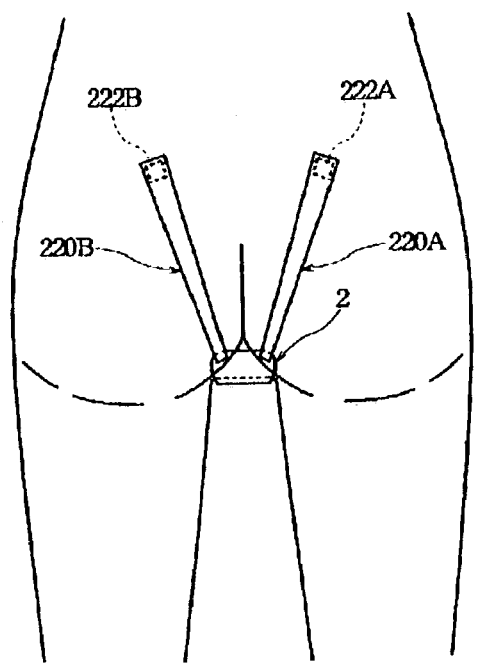
FIG. 7B shows a state where the absorbent article of FIG. 6 is worn, from the back of the wearer's body.

FIGS. 7A and 7B are views showing a state where the absorbent article 200 is worn, wherein FIG. 7A shows the front of the wearer's body and FIG. 7B shows the back of the wearer's body.

The absorbent article 200 is worn as follows: At first, the liquid-receiving surface 50 of the main body portion 2 is brought into contact with the genital organ of a wearer. Then, the two front support members 210A and 210B are stretched forward to fix the pressure sensitive adhesive layers 212A and 212B to the wearer's skin in the lower abdominal region at laterally spaced apart locations, as shown in FIG. 7A. On the other hand, the two rear support members 220A and 220B are stretched rearward to fix the pressure sensitive adhesive layers 222A and 222B to the wearer's skin in the lower lumbar region at laterally spaced apart locations, as shown in FIG. 7B.

Since the pressure sensitive adhesive layers 212A, 212B, 222A and 222B are fixed in the lower abdominal region and the lower lumbar region that are hardly affected by motion of the wearer's body, the main body portion 2 can be prevented from getting out of position due to motion of the wearer's body. In addition to such an advantage, the main body portion 2 can be certainly kept in close contact with the vaginal opening of a wearer because the individual front and rear regions 2A and 2B of the main body portion 2 are fixed such that the left and right halves are pulled in different directions.

Figure 8:
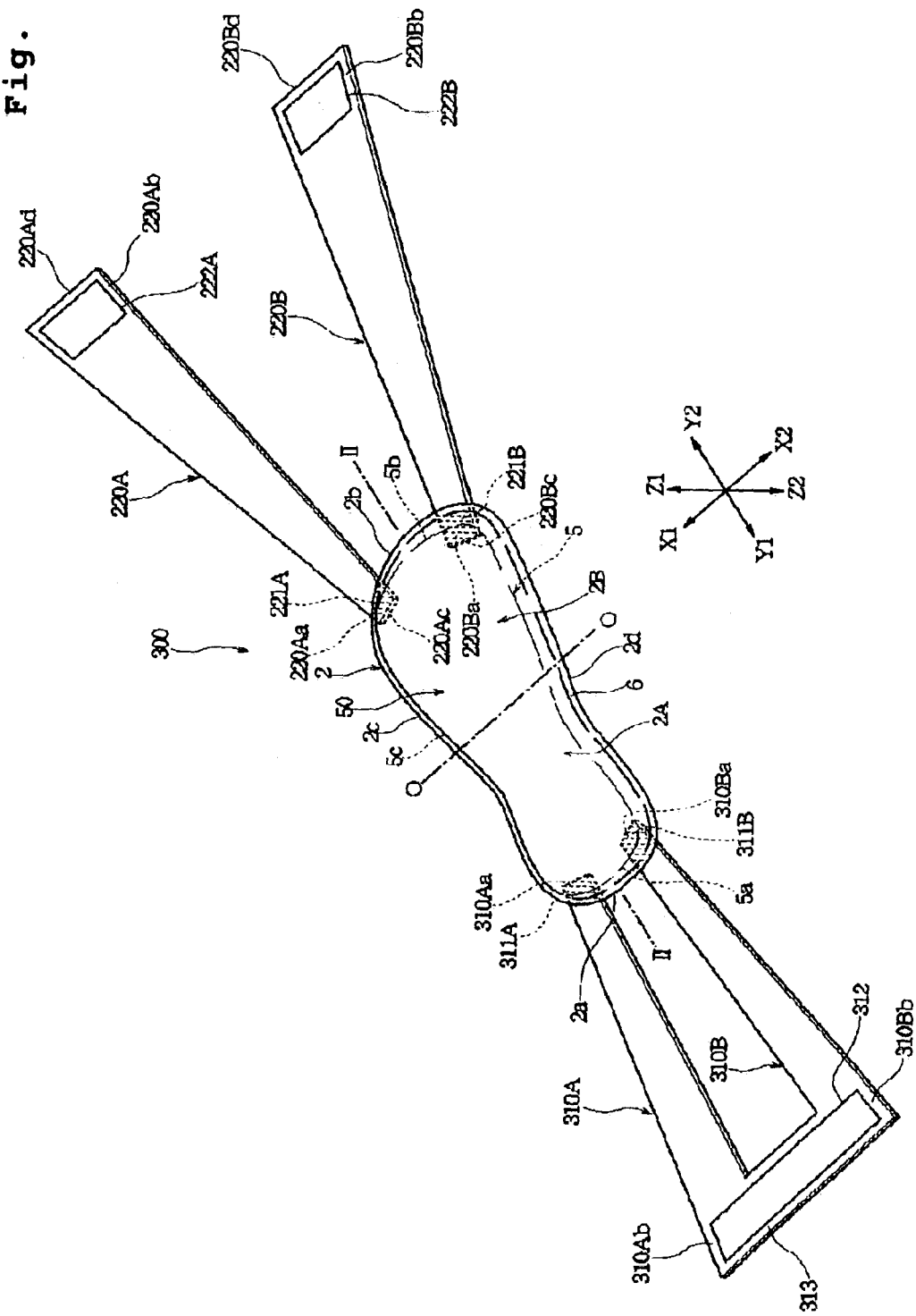
FIG. 8 is a perspective view showing an absorbent article according to a fourth embodiment of the present invention.

FIG. 8 is a perspective view showing an absorbent article 300 according to a fourth embodiment of the present invention. The absorbent article 300 of FIG. 8 has a basic structure similar to that of the absorbent article 200 of FIG. 6, but only the front support member is different in structure. Therefore, the detailed description of the portions having the same constructions as those of the absorbent article 200 of FIG. 6 will be omitted by designating them by the common reference numerals.

The absorbent article 300 of FIG. 8 has two front support members 310A and 310B that are integrally formed. A rear end region 310Aa of the front support member 310A and a rear end region 310Ba of the front support member 310B are fixed on the garment surface of the main body portion 2; and a front end region 310Ab of the front support member 310A and a front end region 310Bb of the front support member 310B are connected to each other, providing a region 313 to be fixed on the wearer's skin (hereinafter referred to as a fixation region 313). On the body surface of the fixation region 313, there is provided a pressure sensitive adhesive layer 312 as means for securing the front support members 310A and 310B to the skin of a wearer.

Since the front support members 310A and 310B of the absorbent article 300 are connected to provide the fixation region 313 that is to be adhered and fixed on the abdominal region, the front support members 310A and 310B can be firmly fixed on the skin.

Figure 9:
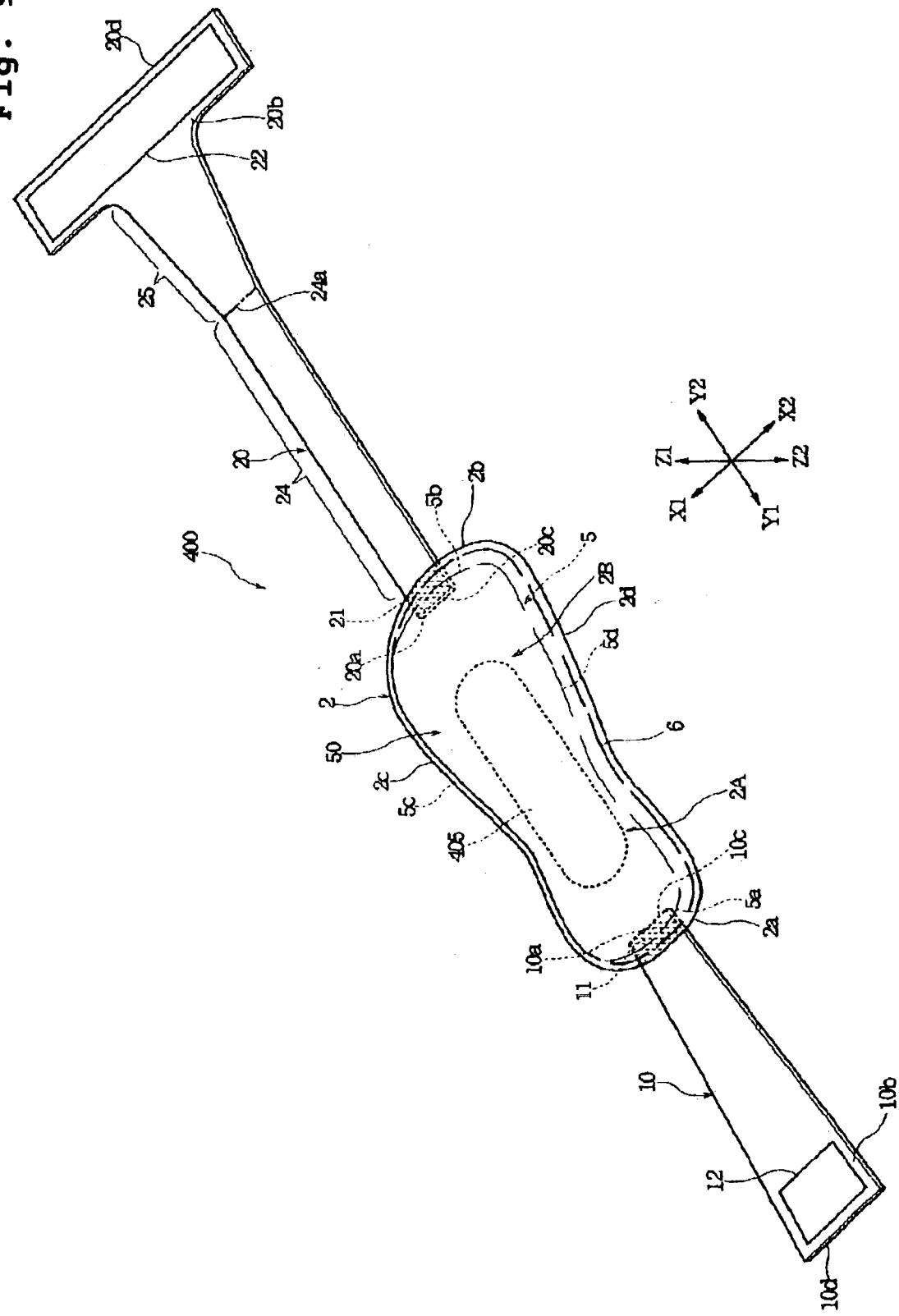
FIG. 9 is a perspective view showing an absorbent article according to a fifth embodiment of the present invention.
Figure 10:
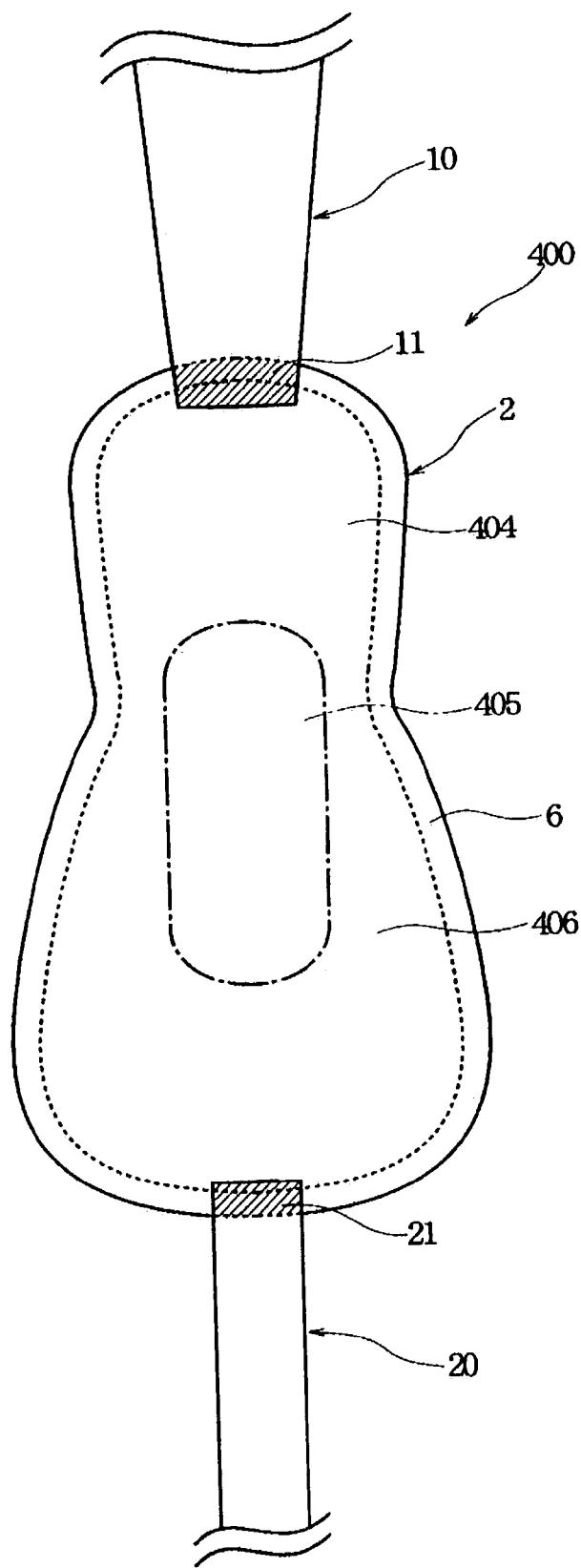
FIG. 10 is a bottom plan view showing the absorbent article of FIG. 9.

FIGS. 9 and 10 show an absorbent article 400 according to a fifth embodiment of the present invention, wherein FIG. 9 is a perspective view and FIG. 10 is a bottom plan view as viewed from the side of a backsheet. The absorbent article 400 has a structure almost similar to that of the absorbent article 1 of FIG. 2. Therefore, the detailed description of the portions having the same constructions as those of the absorbent article 1 of FIG. 2 will be omitted by designating them by the common reference numerals.

In the main body portion 2 of the absorbent article 400, as shown in FIG. 10, there is provided a backsheet 404, of which a liquid permeable region 405 is provided centrally and a liquid impermeable region 406 is provided to surround the liquid permeable region 405.

The absorbent article 400 can be used in combination with another absorbent article such as a sanitary napkin having a backsheet that is impermeable to liquid as a whole. For example, the sanitary napkin is worn by mounting it on a crotch portion of an undergarment, while the absorbent article 400 is worn by fixing it on the skin of the wearer's body so that the absorbent article is positioned between the wearer's skin and the sanitary napkin. In this case, since the absorbent article 400 is in close contact with the genital organ of a wearer, a menstrual blood discharged from the vaginal opening can be firstly absorbed by the main body portion 2 of the absorbent article 400. Then, an amount of menstrual blood in excess of a liquid retention capacity of the main body portion 2 passes through the liquid permeable region 405 of the backsheet 404 and is absorbed and retained by the underlying sanitary napkin. Thus, a large amount of menstrual blood can be retained by the absorbent article 400 and the underlying sanitary napkin while keeping the absorbent article 400 in close contact with the vaginal opening. In addition, the main body portion 2 of the absorbent article 400 can be made compact and thin, thereby facilitating the close contact with the genital organ. Especially since the liquid permeable region 405 is provided centrally of the backsheet 404, the menstrual blood can be certainly introduced from the main body portion 2 to a central portion of the underlying sanitary napkin.

The backsheet 404 may be formed of a sheet prepared by suspending comminuted pulp and/or cotton fibers in air, collecting them on a screen, and then bonding them with a water-soluble resin binder. In an alternative, a sheet comprising polyvinyl alcohol or carboxymethyl cellulose and having liquid passage holes formed centrally thereof may also be used. In another alternative, a liquid permeable sheet may be partially treated to be water repellent or partially covered with a liquid impermeable film or sheet to form the liquid impermeable region 406. In still another alternative, the backsheet 404 may be formed of a sheet comprising a copolymer of ethene and vinyl acetate, regenerated cellulose, polyethylene, polypropylene or polyethylene terephthalate and made permeable to liquid.

Considering use in combination with another absorbent article, the individual components of the absorbent article 400 are preferably formed of water-disintegratable or biodegradable materials so as to facilitate replacement and disposal. As used herein, the term "water-disintegratable" means that when a sheet is put in water, constituent fibers of the sheet can be dispersed. The term "biodegradable" means that fibers can be broken down within a living body or by bacteria.

In order to make the backsheet 404 water-disintegratable, a nonwoven fabric of which fibers are bonded with a water-soluble binder, a nonwoven fabric of which fibers are hydroentangled or a nonwoven fabric of which fibers are bonded by hydrogen bond and/or Van der Waals force may be used as the backsheet 404.

In order to make the topsheet 3 and the backsheet 404 biodegradable, a sheet comprising a polymer of lactic acid, polybutylene succinate, carboxymethyl cellulose or polyvinyl alcohol and having liquid passage holes formed therein may be used as the topsheet 3 and the backsheet 404.

In order to make the absorbent layer 5 biodegradable, a sheet of fibers comprising sodium alginate or starch or an aggregate of particles comprising sodium alginate or starch may be used as the absorbent layer 5, in addition to the above-mentioned materials for the biodegradable topsheet 3 and backsheet 404.

In order to make the front support member 10 and the rear support member 20 biodegradable, a natural rubber (that has cis-1,4-polyisoprene as main component) may be used as the elastic member 31, and a biodegradable nonwoven fabric or film similar to that for the topsheet 3 and the backsheet 404 may be used as the first auxiliary sheet 32 and the second auxiliary sheet 33.

As means for joining the individual components, a water-soluble polyvinyl alcohol may be used as an adhesive. In an alternative, they may be joined by heat welding or hydrogen bonding.

It should be noted that the backsheet of the absorbent article may be permeable to liquid as a whole, although the backsheet 404 of the fifth embodiment is partially permeable to liquid.

Of course, it is possible to provide the absorbent article 400 with the front and rear support members of FIG. 5, FIG. 6 or FIG. 8, in place of the front support member 10 and the rear support member 20.

In the foregoing embodiments, the main body portion 2 is described as having a substantially flat liquid-receiving surface 50. However, the liquid-receiving surface 50 of the main body portion 2 may be protruded toward the genital organ from the first. It is also possible to provide the liquid-receiving surface 50 of the main body portion 2 with a skin-contacting member to fit into the labia.

The individual absorbent articles 1, 100, 200, 300 and 400 may be worn without stretching the support members. Even in such case, since the support members are fixed to the lower abdominal region and the lower lumbar region through the pressure sensitive adhesive layers, the support members can be deformed to stretch in accordance with motion of the wearer's body, thereby absorbing a force caused by the motion of the wearer's body. Therefore, the main body portion 2 hardly gets out of position.

The absorbent article of the present invention is also applicable to a urine-absorbing pad for patients suffering from incontinence, a vaginal discharge absorbing sheet for women or the like.

As has been described hereinabove, the absorbent article of the present invention can be worn by stretching the front and rear support members capable of producing an elastic contractive force and fixing them to the wearer's skin through the securing means provided on the front and rear support members. At this time, the main body portion is forced against the genital organ of a wearer due to the elastic contractive force of the front and rear support members, so that the main body portion comes into close contact with the vaginal opening of a wearer. Since the front and rear support members are fixed to the wearer's skin during use, moreover, even if an undergarment is loosened, stretched or displaced due to motion of the wearer's body, the main body portion can be certainly kept in close contact with the vaginal opening.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An absorbent article comprising
a main body portion having an ability to absorb and retain a liquid;
a front support member extending forward beyond a front edge of the main body portion; and
a rear support member extending rearward beyond a rear edge of the main body portion, the rear support member being separate from the front support member, wherein
the individual front and rear support members produce an elastic contractive force in a stretched state,
the individual front and rear support members are provided with means for securing each support member to the skin of a wearer, and
the front support member has a rear end which is joined to a garment surface of the main body portion, the rear support member has a front end which is joined to the garment surface of the main body portion and spaced a distance rearward from the rear end of the front support member, the rear end of the front support member and the front end of the rear support member are both located in a region ahead of a transversely extending centerline of the main body portion, and the rear support member behind the front end is not joined to the garment surface of the main body portion.

2. An absorbent article comprising:
a main body portion having an ability to absorb and retain a liquid;
a front support member extending forward beyond a front edge of the main body portion; and
a rear support member extending rearward beyond a rear edge of the main body portion, wherein
the individual front and rear support members produce an elastic contractive force in a stretched state, and
the individual front and rear support members are provided with means for securing each support member to the skin of a wearer, wherein
the front support member has a rear end which is joined to a garment surface of the main body portion, the rear support member has a front end which is joined to the garment surface of the main body portion and spaced a distance rearward from the rear end of the front support member, the rear end of the front support member and the front end of the rear support member are both located in a region ahead of a transversely extending centerline of the main body portion, and the rear support member behind the front end is not joined to the garment surface of the main body portion.

3. An absorbent article as set forth in claim 2, wherein the main body portion has a layer for blocking passage of a liquid toward a garment surface of the main body portion.

4. An absorbent article as set forth in claim 2, wherein a garment surface of the main body portion is permeable to liquid, at least in a central region thereof.

5. An absorbent article as set forth in claim 2, wherein the rear support member has a width of equal to or less than 30 mm, within a region of a predetermined length extending rearward from the rear edge of the main body portion.

6. An absorbent article as set forth in claim 5, wherein behind the region of a predetermined length, the rear support member has a region which is gradually widened and provided at a location of a maximum width with the securing means.

7. An absorbent article as set forth in claim 2, wherein at least one of the front and rear support members comprises at least two separate parts individually extending from the main body portion.

8. An absorbent article as set forth in claim 2, wherein when the front and rear support members are fully stretched, a distance between the securing means of the front support member and the securing means of the rear support member increases by at least 1.2 times that before stretch.

9. An absorbent article as set forth in claim 8, wherein when the distance between the securing means of the front support member and the securing means of the rear support member is 1.2 times that before stretch, an elastic contractive force acting between the securing means of the front support member and the securing means of the rear support member is equal to or less than 1960 mN.

10. An absorbent article as set forth in claim 9, wherein when in close contact with the human skin, each securing means has a shear strength of greater than 1960 mN.

11. An absorbent article as set forth in claim 2, wherein each securing means has a peel strength of equal to or less than 0.49 N per 25 mm width.

12. An absorbent article comprising
a main body portion for absorbing and retaining liquid;
a front support member extending forward beyond a front edge of the main body portion; and
a rear support member extending rearward beyond a rear edge of the main body portion,
wherein the front and rear support members both produce elastic contractive force and are provided with securing members, respectively, to attach to the skin of the wearer,
the main body portion has a front region and a rear region with the rear region being wider than the front region, and the front support member is attached at the front region and the rear support member is attached at the rear region, and
the front support member has a forward edge and a rearward edge and has a solid tapered shape with decreasing width from the forward edge to the rearward edge, and the front support member is joined to the main body portion at the rearward edge.

13. An absorbent article comprising:
a main body portion for absorbing and retaining liqiuid;
a front support member extending forward beyond a front edge of the main body portion; and
a rear support member extending rearward beyond a rear edge of the main body portion,
wherein the front and rear support members both produce elastic contractive force and are provided with securing members, respectively, to attach to the skin of the wearer,
the main body portion has a front region and a rear region with the rear region being wider than the front region, and the front support member is attached at the front region and the rear support member is attached at the rear region, and
the rear support member has a fitting region of constant width extending from the rear edge of the main body portion and a region that expands in width from the fitting region; and
the expanding region is attached to a rectangular region which has one of the securing members.

14. An absorbent article comprising:
a main body portion for absorbing and retaining liquid;
a first support member extending forward beyond a front edge of the main body portion; and
a second support member extending rearward beyond a rear edge of the main body portion,
wherein the first and second support member both produce elastic contractive force and are provided with securing members, respectively, to attach to the skin of the wearer,
wherein the first support member has a first forward edge and a first rearward edge and is joined to the main body portion with the first rearward edge spaced inwardly away from the front edge of the main body portion,
wherein the first support member has a solid tapered shape with decreasing width from the first forward edge to the first rearward edge, and the first support member is joined to the main body portion at the first rearward edge,
wherein the second support member has a second forward edge and a second rearward edge and is joined to the main body portion with the second forward edge spaced inwardly away from the rear edge of the main body portion, and
wherein the second support member has a fitting region of constant width extending from the rear edge of the main body portion and has a region that expands in width from the fitting region, and the expanding region is attached to a rectangular region which has one of the securing members, and the second support member is joined to the main body portion at the second forward edge.

15. An absorbent article according to claim 14,
wherein the main body portion has a front region and a rear region with the rear region being wider than the front region, and the first support member is attached at the front region and the second support member is attached at the rear region.

16. An absorbent article according to claim 14,
wherein the main body portion has a front region and a rear region that is wider than the front region and has an hour glass shape.

* * * * *